(12) United States Patent
Proudfoot et al.

(10) Patent No.: US 6,251,118 B1
(45) Date of Patent: Jun. 26, 2001

(54) RADIAL POCKET FORMING AND INSERT POSITIONING INSTRUMENTS, CORNEAL MARKER, AND METHOD FOR USING SAME

(75) Inventors: Robert A. Proudfoot, Santa Clara; John A. Scholl, Danville; Thomas A. Silvestrini, Alamo; Sid Gandionco, Fremont, all of CA (US)

(73) Assignee: KeraVision, Inc., Fremont, CA (US)

( * ) Notice: Subject to any disclaimer, the term of this patent is extended or adjusted under 35 U.S.C. 154(b) by 0 days.

(21) Appl. No.: 09/060,223

(22) Filed: Apr. 14, 1998

Related U.S. Application Data
(60) Provisional application No. 60/043,513, filed on Apr. 14, 1997.

(51) Int. Cl.⁷ ....................................................... A61F 9/00
(52) U.S. Cl. ............................................. 606/166; 606/167
(58) Field of Search .................................. 606/166, 167, 606/170, 107, 190; 623/4, 6

(56) References Cited

U.S. PATENT DOCUMENTS

| | | | |
|---|---|---|---|
| 4,417,579 | * 11/1983 | Soloviev et al. | 128/303 R |
| 4,452,235 | * 6/1984 | Reynolds | 128/1 R |
| 4,671,276 | * 6/1987 | Reynolds | 128/305 |
| 4,688,570 | * 8/1987 | Kramer et al. | 128/305 |
| 4,739,761 | * 4/1988 | Grandon . | |
| 4,766,895 | * 8/1988 | Reynolds | 128/303 R |
| 4,815,463 | * 3/1989 | Hanna | 128/305 |
| 4,844,060 | * 7/1989 | Krumeich | 128/303 R |
| 4,880,017 | * 11/1989 | Soll et al. . | |
| 4,907,587 | * 3/1990 | Fedorov et al. | 606/28 |
| 4,941,093 | * 7/1990 | Marshall et al. | 364/413.01 |
| 4,961,744 | * 10/1990 | Kilmer et al. | 606/166 |

(List continued on next page.)

FOREIGN PATENT DOCUMENTS

| | | | |
|---|---|---|---|
| 43 01 418 A1 | * 3/1995 | (DE) . | |
| 0 541 316 A1 | * 5/1993 | (EP) . | |
| WO 93/01755 | * 2/1993 | (WO) . | |
| WO 93/20763 | * 10/1993 | (WO) . | |
| WO 96/06582 | * 3/1996 | (WO) . | |
| WO 96/40005 | * 12/1996 | (WO) . | |
| WO 97/28759 | * 8/1997 | (WO) | A61F/2/14 |
| WO 98/03136 | * 1/1998 | (WO) . | |

OTHER PUBLICATIONS

P.A. Gonchar, et al., "Interlayer Refraction Tunnel Keratoplasty in Correction of Myopia and Astigmatism", Vestnik oftal'mologii, vol. 104, No. 4, 1988, pp. 25–30.*

N.M. Sergienko, et al., "Meridional Wedge Keratoplasty in Myopia", Oftal'mologicheskii zhurnal, No. 3, 1986, pp, 155–157.*

*Primary Examiner*—Michael Buiz
*Assistant Examiner*—Lien Ngo
(74) *Attorney, Agent, or Firm*—Harry J. Macey; KeraVision, Inc.

(57) ABSTRACT

Instruments and methods are provided which permit a surgeon to implant multiple radial inserts within a patient's cornea through one or more incisions made into the cornea. Instruments provided by the invention include a corneal marker, a radial pocket-forming instrument, and a positioning instrument. In one method provided by the invention, the surgeon uses the corneal marker to mark the patient's cornea with an incision mark, radial pocket marks, and circumferential channels marks simultaneously. The surgeon forms clockwise and counter-clockwise intrastromal circumferential channels through a single incision into the cornea, and then the surgeon inserts the radial pocket-forming instrument through the incision and into one of the circumferential channels to form radial pockets beneath the radial pocket marks. The surgeon inserts radial intrastromal inserts through the incision and into the circumferential channels and positions them within the radial pockets using the positioning instrument.

14 Claims, 11 Drawing Sheets

U.S. PATENT DOCUMENTS

| | | | | |
|---|---|---|---|---|
| 5,300,118 | * | 4/1994 | Silvestrini et al. | 623/5 |
| 5,318,047 | * | 6/1994 | Davenport et al. | 128/898 |
| 5,323,788 | * | 6/1994 | Silvestrini | 128/897 |
| 5,403,335 | * | 4/1995 | Loomas et al. | 606/161 |
| 5,405,384 | * | 4/1995 | Silvestrini et al. | 623/5 |
| 5,425,727 | * | 6/1995 | Koziol | 606/5 |
| 5,466,260 | * | 11/1995 | Silvestrini et al. | 623/5 |
| 5,571,124 | * | 11/1996 | Zelman | 606/166 |
| 5,653,725 | * | 8/1997 | Simon et al. | 606/166 |

* cited by examiner

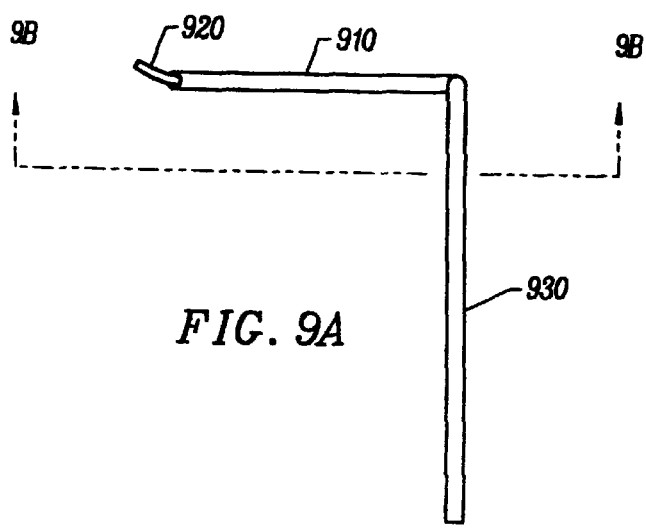
FIG. 9A
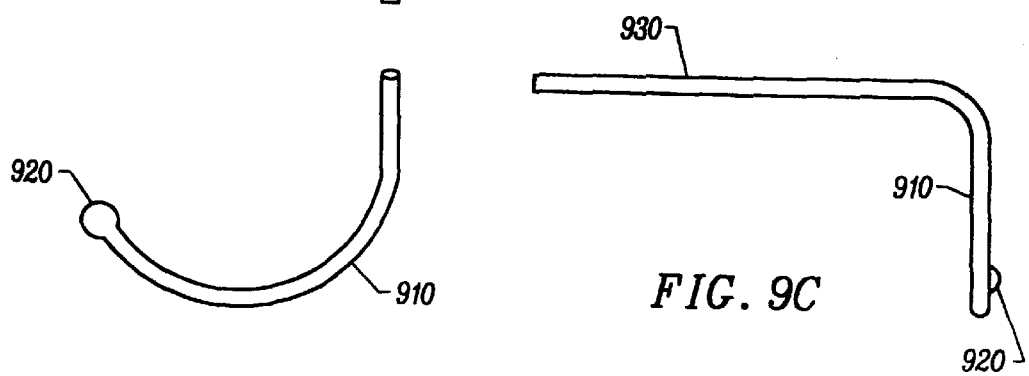
FIG. 9B
FIG. 9C

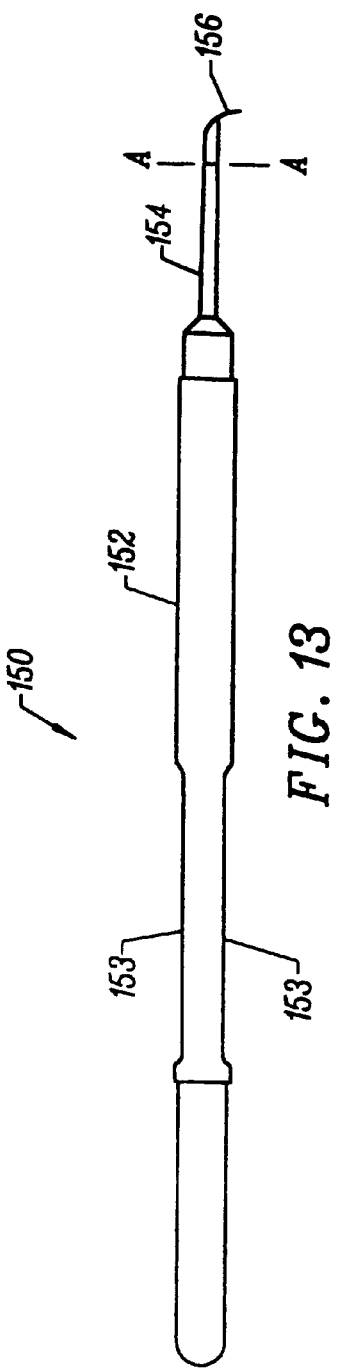
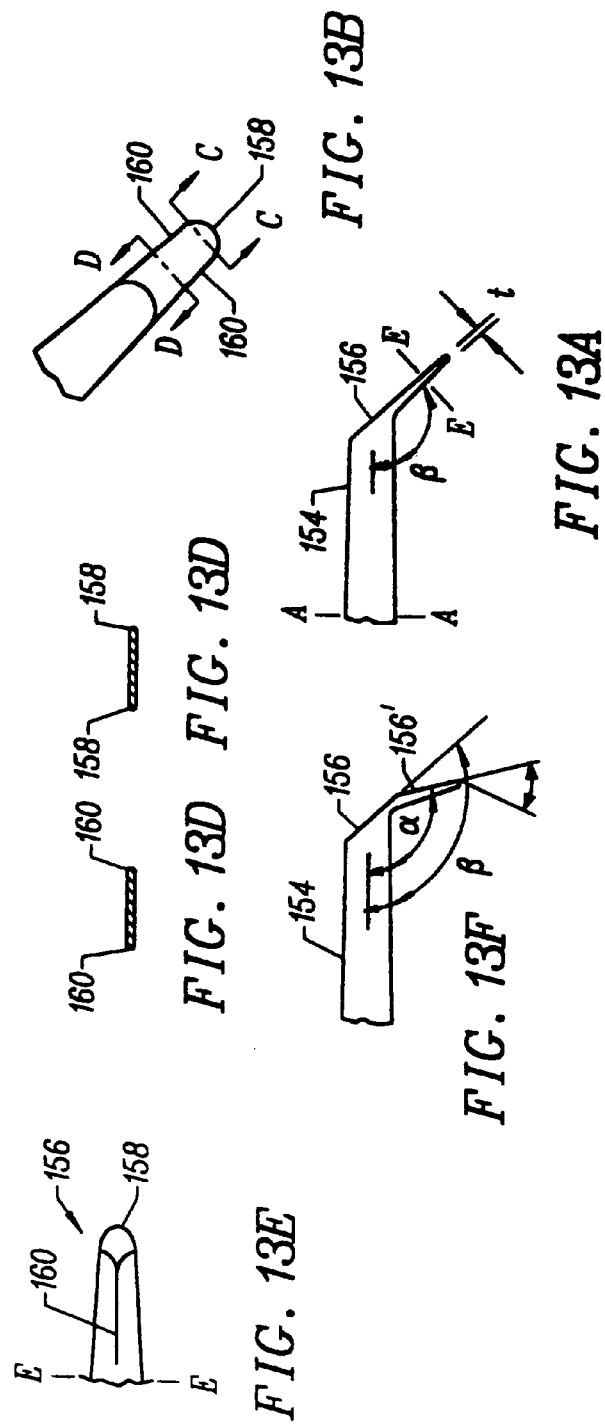
FIG. 13
FIG. 13A
FIG. 13B
FIG. 13D
FIG. 13E
FIG. 13F

RADIAL POCKET FORMING AND INSERT POSITIONING INSTRUMENTS, CORNEAL MARKER, AND METHOD FOR USING SAME

CROSS-REFERENCE TO RELATED APPLICATIONS

This application claims priority to U.S. Provisional Application No. 60/043,513, filed Apr. 14, 1997, which is incorporated by reference herein in its entirety.

BACKGROUND AND SUMMARY OF THE INVENTION

Field of the Invention

The invention provides surgical instruments that facilitate insertion of radial inserts within the cornea of a patient's eye. The invention also provides a method for implanting radial intracorneal inserts in order to correct such deficiencies in the patient's vision as hyperopia, myopia, and/or astigmatism.

Intracorneal Inserts

Anomalies in the overall shape of the eye can cause visual disorders. Hyperopia ("farsightedness") occurs when the front-to-back distance in the eyeball is too short. In such a case, parallel rays originating greater than 20 feet from the eye focus behind the retina. Although minor amounts of hyperopia can be resolved in the human eye by a muscular action known as "accommodation", aging often compromises the ability of the eye adequately to accommodate. In contrast, when the front-to-back distance of eyeball is too long, myopia ("nearsightedness") occurs and the focus of parallel rays entering the eye occurs in front of the retina. Astigmatism is a condition which occurs when the parallel rays of light do not focus to a single point within the eye, but rather have a variable focus due to the fact that the cornea refracts light in a different meridian at different distances. Some degree of astigmatism is normal, but where it is pronounced, the astigmatism must be corrected.

Hyperopia, myopia, and astigmatism are usually corrected by glasses or contact lenses. Surgical methods for the correction of such disorders are known. Such methods include radial keratotomy (see, e.g., U.S. Pat. Nos. 4,815,463 and 4,688,570) and laser corneal ablation (see, e.g., U.S. Pat. No. 4,941,093).

Another method for correcting those disorders is through the implantation of polymeric rings (intrastromal corneal rings or "ICR's") in the eye's corneal stroma to change the curvature of the cornea. Previous work involving the implantation of polymethylmethacrylate (PMMA) rings, allograft corneal tissue, and hydrogels is well documented. One of the ring devices involves a split ring design which is inserted into a channel previously dissected in the stromal layer of the cornea. A minimally invasive incision is used both for producing the channel and for inserting the insert. See, for instance, the use of PMMA intrastromal rings in U.S. Pat. Nos. 4,452,235 to Reynolds; 4,671,276 to Reynolds; 4,766,895 to Reynolds; and 4,961,744 to Kilmer et al. These documents suggest only the use of circumferential ICR's.

Instead of inserting polymeric rings or arcs into the cornea, radial intracorneal inserts having a significant radial or meridional dimension may be placed within the cornea to adjust corneal curvature and thereby correct or improve vision abnormalities such as hyperopia. This invention provides instruments and a method for implanting such radial intracorneal inserts.

Method and Instruments of this Invention

The invention provides surgical instruments that facilitate insertion of radial inserts within the cornea of a patient's eye. The invention also provides a method for implanting radial intracorneal inserts in order to correct such deficiencies in the patient's vision as hyperopia, myopia, and/or astigmatism.

One method provided by the invention is a method for preparing the cornea of a patient's eye to receive a radial intracorneal insert. In this method, a surgeon makes an incision into the cornea and forms a circumferential channel within the cornea by inserting a channel-forming instrument through the incision. The surgeon also forms a radial pocket within the patient's cornea such that an end of the radial pocket connects to the circumferential channel. The surgeon can place a radial intracorneal insert into the radial pocket, and the surgeon can also place a circumferential insert into the circumferential channel, if desired.

The invention also provides various instruments that the surgeon uses to mark the patient's eye, to form radial pockets, and to position radial intracorneal inserts within radial pockets. A corneal marker is used to place ink-marks on the surface of the patient's cornea to mark various regions where surgery is to be performed. One corneal marker has a number of individual markers incorporated into the marker. This corneal marker has an incision marker, which marks the site on the cornea where the incision mentioned above is to be made; a radial pocket marker, which marks the site on the cornea where a radial pocket is to be formed; and a positioner for positioning the incision marker and the radial pocket marker in the desired locations on the patient's cornea.

A radial-pocket forming instrument is used to form radial pockets into which radial intracorneal inserts are placed. One radial pocket-forming instrument provided by this invention is designed to be inserted into the circumferential channel formed by the method described above to create one or more radial pockets. This radial pocket-forming instrument has a tissue separator positioned on the side of a generally arcuate member that is inserted into the circumferential channel. The radial pocket-forming instrument is inserted into the circumferential channel through the incision made in the patient's cornea and is positioned so that the tissue separator is adjacent to a mark made by the radial pocket marker of the corneal marker described above. The tissue separator is then rotated or translated sideways so that the tissue separator contacts a sidewall of the circumferential channel and pushes between stroma, forming a radial pocket in the patient's cornea.

The surgeon uses a positioning instrument to maneuver a radial intracorneal insert and place the insert within a radial pocket. A radial intracorneal insert is inserted into the circumferential channel through the incision made in the patient's cornea and is positioned so that the radial intracorneal insert is adjacent to a radial pocket. The positioning instrument, which has also been inserted into the circumferential channel through the incision, has a generally arcuate member of a size and shape that fits within the circumferential channel formed within the patient's cornea and also has a tip positioned at or near one end of the generally arcuate member. The tip is used to contact a radial intracorneal insert and move the insert so that an end of the insert enters the radial pocket and seats within the pocket.

The invention is described in greater detail below. Among other factors, the invention is based on the inventors' technical finding that the methods and instruments of this invention which form radial pockets into which radial intracorneal inserts are implanted provide quick and reliable insertion of radial intracorneal inserts within a patient's eye to correct vision deficiencies. Few incisions into the cornea and through the stroma are needed, and thus little suturing is required, and the chance of eye infection is reduced. These technical findings and advantages and others are apparent from the discussion herein.

BRIEF DESCRIPTION OF THE FIGURES

The figures and "Detailed Description" provide examples of devices and methods of the invention and are not to be construed as limiting the scope of the invention, and the claims are to be given their broadest interpretation within the spirit of the invention described herein.

FIGS. 9A, 9B and 9C illustrate a radial pocket-forming instrument.

FIGS. 11–14 illustrate surgical instruments in the art useable with the invention.

DETAILED DESCRIPTION OF THE PREFERRED EMBODIMENT

A brief discussion of the physiology of a human eye precedes the discussion of the preferred embodiment of the invention in order to explain the functional relationship of these intracorneal inserts or segments to the eye.

Figure 1:
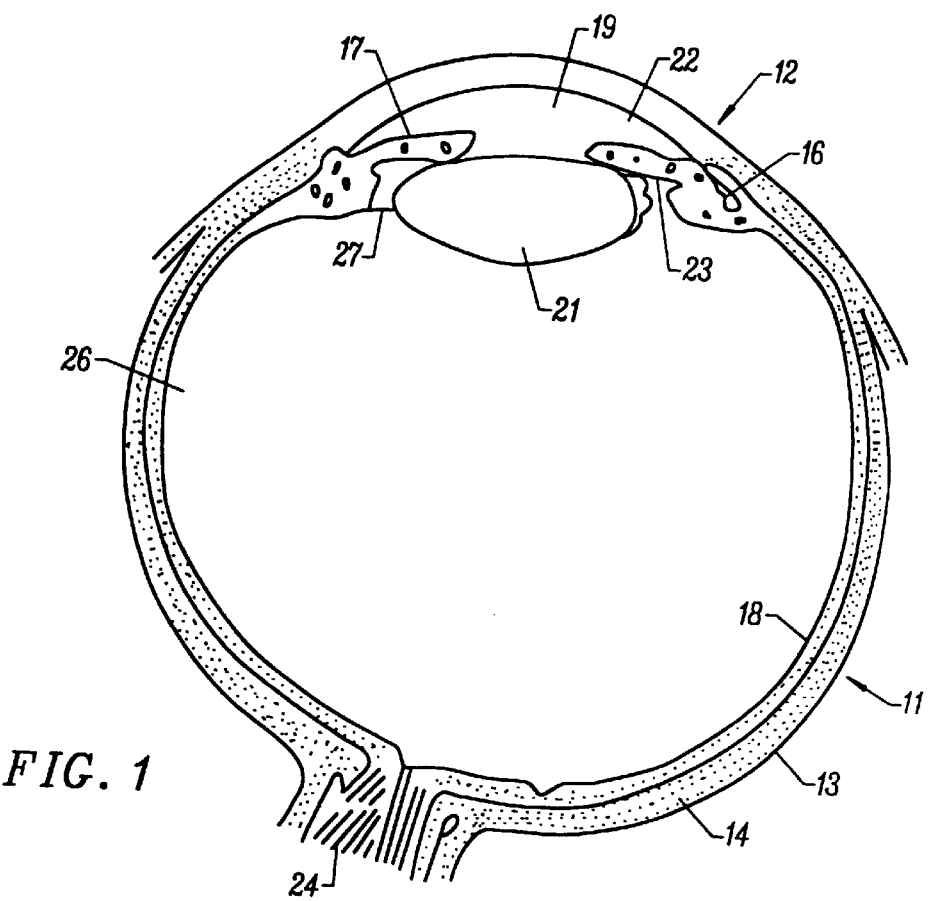
FIGS. 1 and 2 illustrate the physiology of a human eye.

FIG. 1 shows a horizontal cross-section of the eye with the globe (11) of the eye resembling a sphere with an anterior bulged spherical portion representing the cornea (12).

The globe (11) of the eye consists of three concentric coverings enclosing the various transparent media through which the light must pass before reaching the light-sensitive retina (18). The outermost covering is a fibrous protective portion the posterior five-sixths of which is white and opaque and called the sclera (13), and sometimes referred to as the white of the eye where visible to the front. The anterior one-sixth of this outer layer is the transparent cornea (12).

A middle covering is mainly vascular and nutritive in function and is made up of the choroid, ciliary body (16), and iris (17). The choroid generally functions to maintain the retina (18). The ciliary body (16) is involved in suspending the lens (21) and accommodation of the lens. The iris (17) is the most anterior portion of the middle covering of the eye and is arranged in a frontal plane. It is a thin circular disc similar in function to the diaphragm of a camera, and is perforate near its center by a circular aperture called the pupil (19). The size of the pupil varies to regulate the amount of light which reaches the retina (18). It contracts also to accommodation, which serves to sharpen the focus by diminishing spherical aberration. The iris divides the space between the cornea (12) and the lens (21) into an anterior chamber (22) and the posterior chamber (23). The innermost portion of covering is the retina (18), consisting of nerve elements which form the true receptive portion for visual impressions.

The retina (18) is a part of the brain arising as an outgrowth from the fore-brain, with the optic nerve (24) serving as a fiber tract connecting the retina part of the brain with the fore-brain. A layer of rods and cones, lying just beneath a pigmented epithelium on the anterior wall of the retina serve as visual cells or photoreceptors which transform physical energy (light) into nerve impulses.

The vitreous body (26) is a transparent gelatinous mass which fills the posterior four-fifths of the globe (11). At its sides it supports the ciliary body (16) and the retina (18). A frontal saucer-shaped depression houses the lens.

The lens (21) of the eye is a transparent bi-convex body of crystalline appearance placed between the iris (17) and vitreous body (26). Its axial diameter varies markedly with accommodation. A ciliary zonule (27), consisting of transparent fibers passing between the ciliary body (16) and lens (21) serves to hold the lens (21) in position and enables the ciliary muscle to act on it.

Referring again to the cornea (12), this outermost fibrous transparent coating resembles a watch glass. Its curvature is somewhat greater than the rest of the globe and is ideally spherical in nature. However, often it is more curved in one meridian than another giving rise to astigmatism. A central third of the cornea is called the optical zone with a slight flattening taking place outwardly thereof as the cornea thickens towards its periphery. Most of the refraction of the eye takes place through the cornea.

Figure 2:
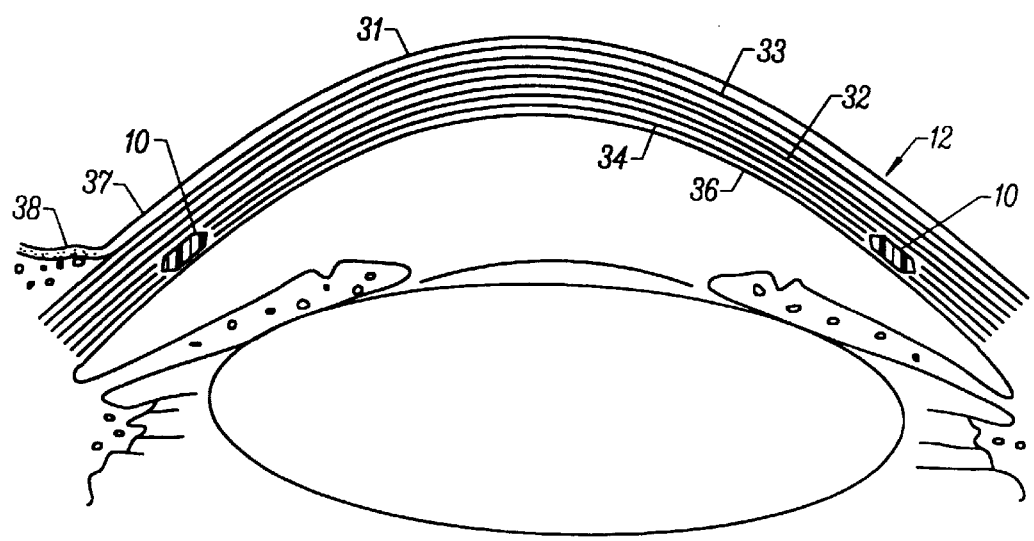

FIG. 2 is a more detailed drawing of the anterior portion of the globe showing the various layers of the cornea (12) making up the epithelium (31). Epithelial cells on the surface thereof function to maintain transparency of the cornea (12). These epithelial cells are rich in glycogen, enzymes and acetylcholine and their activity regulates the corneal corpuscles and controls the transport of water and electrolytes through the lamellae of the stroma (32) of the cornea (12).

An anterior limiting lamella (33), referred to as Bowman's membrane or layer, is positioned between the epithelium (31) and the stroma (32) of the cornea. The corneal stroma (32) are made up of lamellae having bands of fibrils parallel to each other and crossing the whole of the cornea. While most of the fibrous bands are parallel to the surface, some are oblique, especially anteriorly. A posterior limiting lamella (34) is referred to as Descemet's membrane. It is a strong membrane sharply defined from the stroma (32) and resistant to pathological processes of the cornea. The endothelium (36) is the most posterior layer of the cornea and consists of a single layer of cells. The limbus (37) is the transition zone between the conjunctiva (38) and sclera on the one hand and the cornea (12) on the other.

The invention provides a method for placing a radial intracorneal insert within a patient's eye consisting of two basic steps: (1) preparing the patient's cornea to receive a radial intracorneal insert; and (2) inserting the radial intracorneal insert into the patient's cornea. Each of these steps is discussed below.

Preparing the Cornea to Receive a Radial Intracorneal Insert

Figure 3:
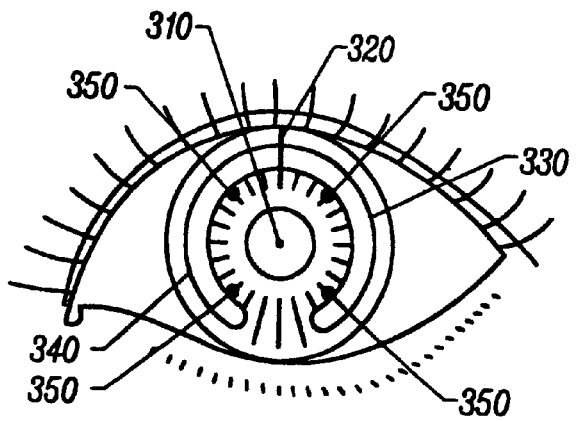
FIG. 3 illustrates markings made by a corneal marker.

One method that can be used generally to prepare the cornea is described in U.S. Pat. No. 5,300,118 to Silvestrini et al, issued Apr. 5, 1994, which patent is incorporated herein by reference in its entirety. As illustrated in FIG. 3, the surgeon places a center mark 310 at the geometric center of the cornea using a blunt instrument and an operating microscope or other comparable technique that accurately marks the center of the cornea. The surgeon next aligns a corneal marker (such as the one illustrated in FIG. 7, which is described in more detail infra) with the center mark and presses the corneal marker onto the cornea, marking the cornea with an incision mark 320 and with radial pocket marks 350. The surgeon optionally also uses a second corneal marker having clockwise and counter-clockwise circumferential channel markers to form clockwise 330 and counter-clockwise 340 circumferential channel marks, if desired. (The radial and circumferential marks may also be formed by one marker that has both radial and circumferential markers.)

Figure 4:
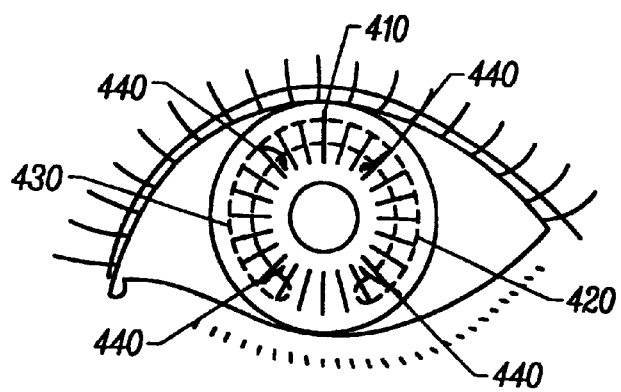
FIG. 4 shows an incision into the cornea as well as circumferential channels and radial pockets formed between stroma.

The surgeon makes an incision (410 of FIG. 4) into the cornea at the incision mark 320, cutting through some but not all of the stroma. The surgeon next forms clockwise 420 and counter-clockwise 430 circumferential channels between stroma.

Circumferential channels are formed using any of a number of methods. One method is disclosed in our U.S. Pat. No. 5,403,335, which is incorporated herein by reference in its entirety. In this method, a vacuum centering guide is positioned on the cornea using the centering mark on the cornea, and a vacuum of approximately 10–27 in. Hg is drawn to hold the vacuum centering guide on the eye. Small "starter" pockets are formed at the base of the incision perpendicular to the incision and in the direction that the circumferential channels are to be formed. The surgeon inserts a clockwise dissector blade into the vacuum centering guide, and the surgeon inserts a blunt-tipped instrument into one of the small "starter" pockets, lifts the corneal tissue, and inserts the tip of the dissector blade into the starter pocket. The surgeon then rotates the dissector blade, which separates stroma and forms a clockwise circumferential channel between stroma. The surgeon removes the clockwise dissector blade and repeats the procedure using the counter-clockwise dissector blade to form a counter-clockwise circumferential channel. Separate, unjoined circumferential channels of any arc length or a continuous 360° channel can be formed using this method.

The surgeon forms a radial pocket 440 by inserting a radial pocket-forming instrument (such as the one illustrated in FIG. 9, which is described in more detail infra) through the single incision and into the circumferential channel a sufficient distance that a tissue separator (such as a blade) on the instrument either is under one of the radial pocket marks 350 on the cornea that crosses the circumferential channel or is adjacent to one of the radial pocket marks that ends at or near the circumferential channel. The surgeon rotates the radial pocket-forming instrument or translates the instrument laterally so that the blade engages the sidewall of the circumferential channel and separates stroma to form a radial pocket connected to the circumferential channel and located beneath the radial pocket mark. The length, width, and shape of the pocket are determined by the size and shape of the blade. The surgeon rotates or translates the radial pocket-forming instrument in the opposite direction to remove the blade from the radial pocket and repositions the blade adjacent to another radial pocket mark to form another radial pocket. When all radial pockets have been formed, the radial pocket-forming instrument is withdrawn from the circumferential channel. The cornea is thus prepared to receive an intracorneal insert.

The method of preparing a cornea to receive an intracorneal insert as described above has significant advantages over previous methods. Only one incision into the cornea needs to be made. The remaining surgery to form the circumferential channel and the radial pocket and to implant the radial insert in the radial pocket is performed through the single incision into the cornea. Consequently, only one site through which foreign matter can gain entry to the eye must heal. Surgery proceeds rapidly, and suturing of the single incision is performed quickly. The likelihood of infection is reduced, and the likelihood of rapid healing of the epithelium is increased.

Inserting the Radial Intracorneal Insert into the Cornea

Figure 5:
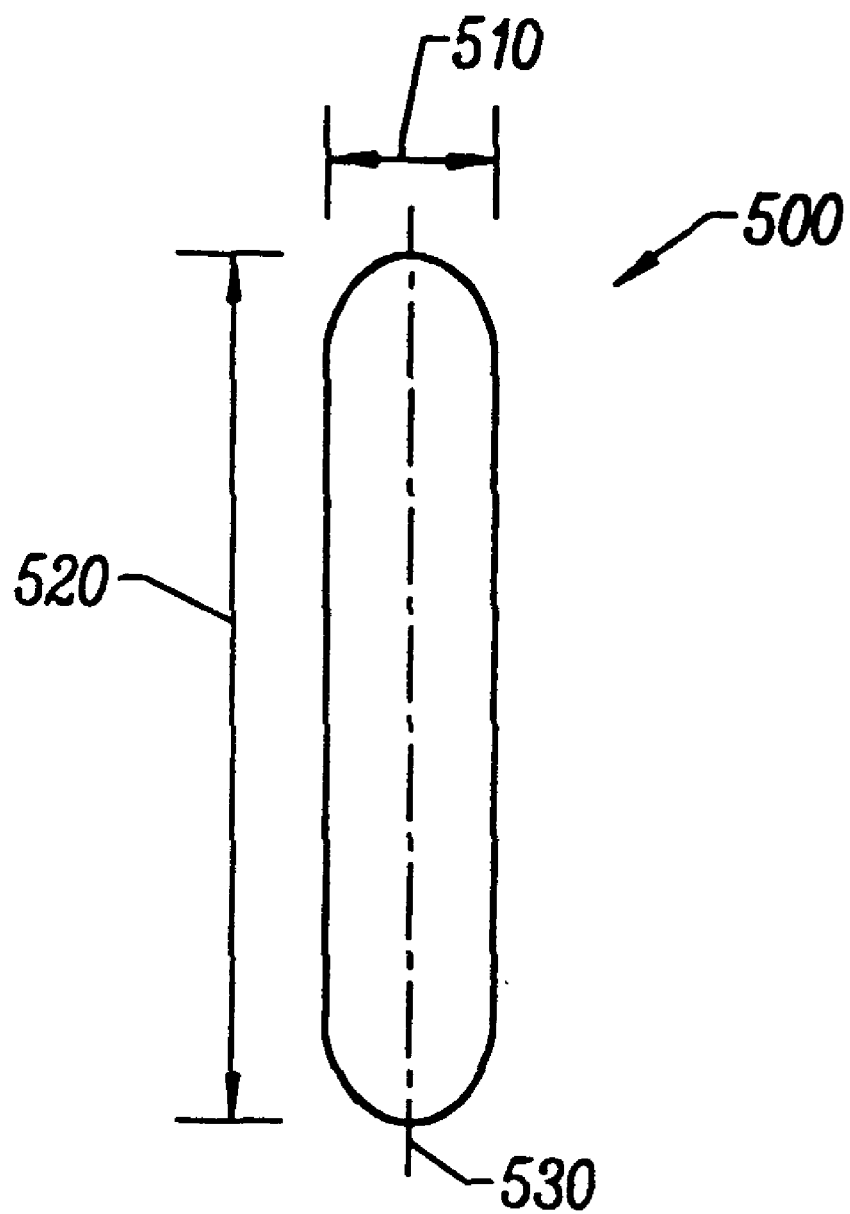
FIG. 5 illustrates a radial intracorneal insert.

Once the surgeon has prepared a cornea to receive an intracorneal insert as described above, the surgeon places a radial insert 500 of FIG. 5 into the circumferential channel through the incision in the cornea. The radial inserts may be introduced into the channel by way of the incision in any appropriate manner. For example, the insert may be grasped and manipulated through the incision and into the channel using standard micro-forceps. Preferably, the forceps are constructed with tip ends having enhanced gripping features to positively hold the insert against sliding or rotation relative to the tip ends. Such features may include recesses or indentations adapted to receive a portion of the insert, protuberences, gripping teeth, or other such features constructed to positively hold the insert. The exact configuration depends upon the shape of the insert and the preference of the surgeon.

The radial insert illustrated in FIG. 5 is an oblong polymeric piece which has a width 510 about equal to the width of the radial pocket and a length 520 about equal to the sum of the length of the radial pocket and the width of the circumferential channel. Since this radial insert is longer than the width of the channel, the insert is best maneuvered within the circumferential channel by inserting the insert length-wise through the incision and into the circumferential channel and keeping the major axis of the insert approximately parallel to the sidewalls of the circumferential channel as the insert is manipulated within the circumferential channel.

Figure 6:
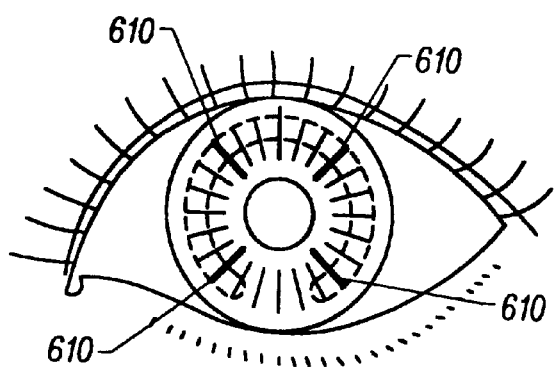
FIG. 6 shows the eye with radial intracorneal inserts implanted in radial pockets.

The surgeon uses an instrument to push or pull the radial insert to a position adjacent to a radial pocket, and subsequently the surgeon uses the same instrument or another positioning instrument (such as the one illustrated in FIG. 10, which is described in greater detail infra) to maneuver one end of the radial insert into the radial pocket and to maneuver the other end of the radial insert against the sidewall of the circumferential channel that is opposite to the radial pocket. If more than one radial pocket is connected to a circumferential channel, the surgeon places the first radial insert into the radial pocket that is located farthest from the single incision into the cornea. The surgeon places the next radial insert into the radial pocket that is second farthest from the single incision, and this process is repeated until the radial pockets have been filled with radial inserts 610, as shown in FIG. 6.

The surgeon can insert short circumferential inserts between adjacent radial inserts, if desired. The short circumferential inserts allow the surgeon to further adjust the shape of the cornea and correct deficiencies in the patient's vision. In one method, the surgeon places a radial insert as discussed above into the farthest radial pocket from the single incision, and next the surgeon places a circumferential insert into the circumferential channel so that the circumferential insert abuts the radial insert. The circumferential insert is shorter than or the same length as the distance in the circumferential channel between adjacent radial pockets. The surgeon then alternately places a radial insert into the next farthest radial pocket and places a circumferential insert into the circumferential channel as described above until the surgeon has completed the surgical procedure. In another method, the surgeon inserts short radial inserts having lengths about equal to the lengths of the radial pockets into which the radial inserts are implanted. A single circumferential insert is placed into the circumferential channel to both hold the radial inserts in their pockets and to further reshape the patient's cornea. The number of inserts and the size and shape of each circumferential insert and radial insert are determined by the amount of reshaping of the cornea that is needed to provide a spherically-shaped cornea in the patient's eye. The initial opening is then closed by use of a suture, glue, staple, or by electrosurgical welding.

Alternatively an introducer apparatus capable of holding and controllably inserting one or more inserts into the channel may be used. Suitable instruments for placing an insert into an intracorneal channel can be found in "CORNEAL IMPLANT INTRODUCER AND METHOD OF USE", filed on Dec. 18, 1997 (U.S. application Ser. No. 08/993,594), the entirety of which is incorporated herein by reference.

While the present invention discloses inserting and positioning radial inserts through a circumferential channel, radial inserts may also be inserted through one or more individual incisions and positioned directly into a radial pocket. Among other things, this technique is described in "RADIAL INTRASTROMAL CORNEAL INSERT AND A METHOD OF INSERTION", filed on Dec. 18, 1997 (U.S. application Ser. No. 08/993,696), the entirety of which is incorporated herein by reference.

Instruments of this Invention

Corneal Marker

Turning now to the specifics of the instruments discussed above, the corneal marker used to make the marks on the cornea to guide subsequent surgical procedures may be constructed in a number of ways. A corneal marker may be provided which has an incision marker, clockwise and counterclockwise channel markers, and radial pocket markers which form their corresponding marks simultaneously when the corneal marker is pressed against the patient's eye.

Alternatively, multiple corneal markers can be used to form the incision mark, the clockwise and counterclockwise circumferential channel marks, and the radial pocket marks which aid the surgeon during surgery. For example, two corneal markers can be used to form the desired marks. One corneal marker may have an incision marker, clockwise and counterclockwise channel markers, and a reticule or sight to enable the corneal marker to be aligned to the center mark (310) of the patient's cornea. The second marker may have radial pocket markers and a reticule or sight. Each corneal marker is individually aligned with the center mark (310) and pressed against the patient's cornea to form the desired marks. The combined incision/circumferential channel markers is usually pressed against the cornea before any vacuum centering guide is placed thereon so that the surgeon can easily make the initial incision into the cornea. After the vacuum centering guide is placed on the cornea, the surgeon inserts the second corneal marker into the vacuum guide and presses it against the patients cornea to from radial marks on the cornea to guide surgery.

Figures 7A, 7B:
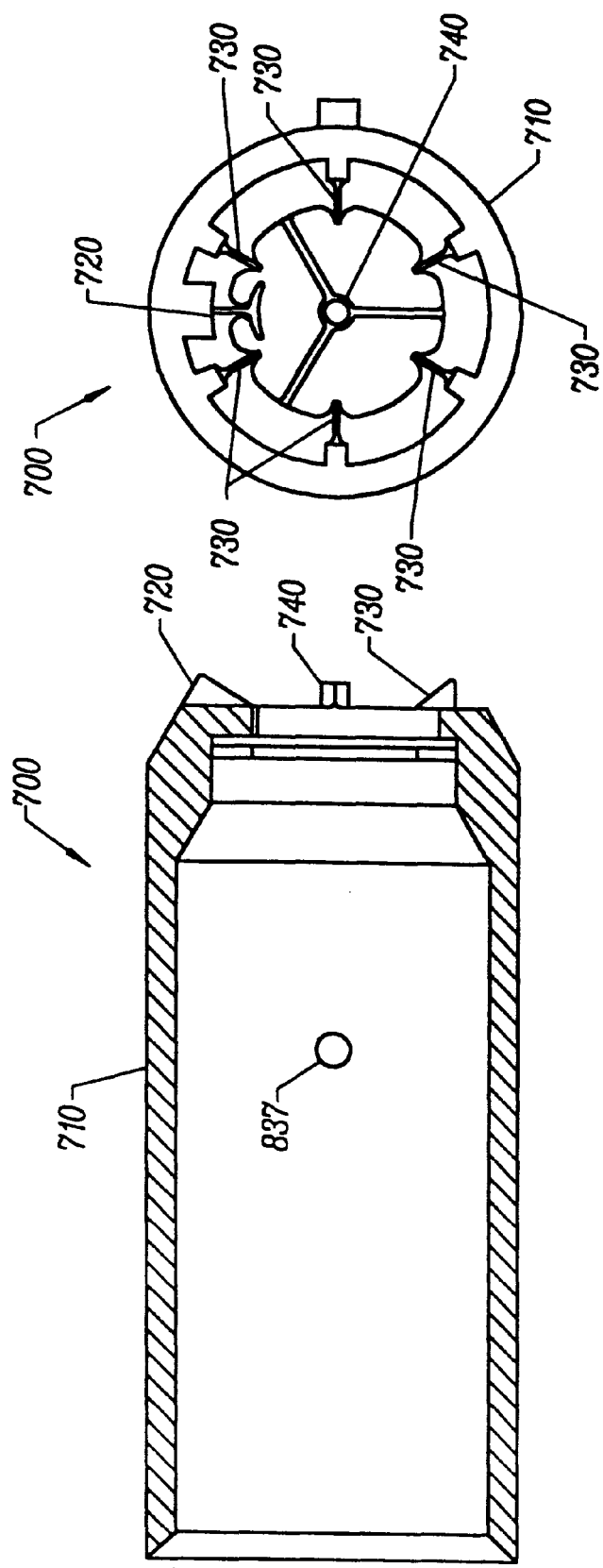
FIGS. 7 and 8 illustrate corneal markers.

A suitable corneal marker is illustrated in FIGS. 7A–7B. FIG. 7A is a side view and FIG. 7B is an end view of corneal marker (700). This corneal marker has a housing (710) to which an incision marker, radial pocket markers, channel or pocket markers, and a positioner may be attached as desired. The incision marker and radial pocket markers are inked with a dye prior to aligning the marker to the center of the patient's cornea and pressing the marker to the patient's cornea to mark it with appropriate markings.

Figure 8A:
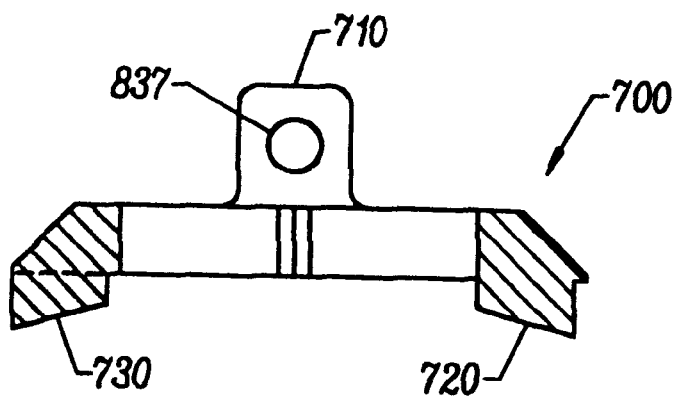
Figure 8B:
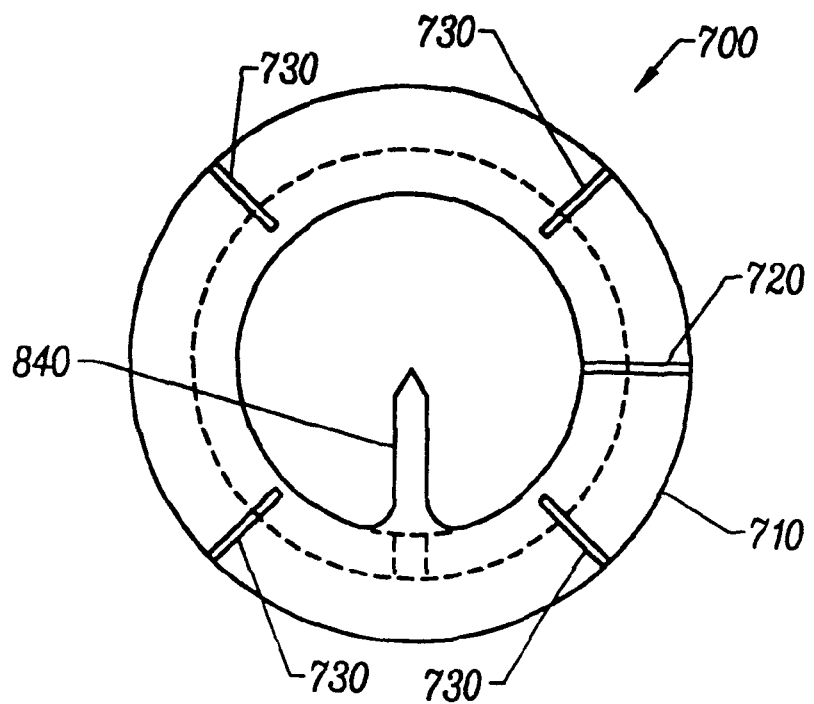

The positioner (740) is used to assure that any marks placed onto the cornea are placed at positions on the patient's cornea where the surgeon has specified that surgery will occur. Usually, the positioner is used to align the corneal marker with the center of the patient's cornea. This arrangement may be used in conjunction with a vacuum centering guide if desired. For the hand-held corneal marker (800) illustrated in FIGS. 7 and 8, a reticule 740 or sight (840) or other positioning means is used to position the corneal marker e.g. over a centering mark placed on the patient's cornea.

Radial pocket markers (730) mark the locations of radial pockets that will be formed within the patient's cornea. Radial pocket markers can be spaced equidistantly from adjacent radial pocket markers. Consequently, a four-pocket corneal marker has four radial pocket markers spaced 90° from one another; a five-pocket corneal marker has five radial pocket markers spaced 72° from one another, a six-pocket corneal marker has six radial pocket markers spaced 60° from one another, a seven-pocket corneal marker has seven radial pocket markers spaced about 51° from one another, an eight-pocket corneal marker has eight radial pocket markers spaced about 45° from one another, and so forth. Any number of radial pocket markers can be incorporated into the corneal marker, from one to ten or more.

The incision marker (720) is the "I" or "H" shaped marker of FIG. 7B which marks the site of the single radial incision to be made into the cornea from outside of the cornea. The incision marker can be located equidistant between adjacent radial pocket markers. For example, if the corneal marker has four equidistantly-spaced radial pocket markers, the incision marker is located 45° from its two adjacent radial pocket markers.

The corneal marker may have more than one incision marker, if desired. For example, if two unconnected circumferential channels are to be formed in the patient's cornea, the corneal marker will usually have at least two incision markers that provide the needed incision marks without having to align the corneal marker to the center of the patient's cornea and mark the cornea a second time.

The hand held markers (700) are constructed to allow the attachment of a handle to allow easy manipulation by the surgeon. The instrument handle may have any comfortable shape and position that allows the surgeon to align the marker against the eye to apply sufficient pressure to mark the cornea. The hand-held markers (700) may be provided with handle mounting flanges 710 to which an instrument handle (not shown) may be attached using mounting holes (837).

The corneal marker can also have one or more circumferential channel markers which mark regions on the cornea where one or more circumferential channels will be formed. When the corneal marker has one or more circumferential channel markers, radial pocket markers can terminate on one side or the other of the circumferential channel marker, so that the radial pocket marks point generally toward the patient's pupil or point generally away from the patient's pupil. Or, the radial pocket markers can cross the circumferential channel markers to provide generally "X"- or cross-shaped marks. It is not necessary for the corneal marker to have a circumferential channel marker. For example, when clockwise and counter-clockwise dissector blades as described above and in U.S. Pat. No. 5,403,335 are used to form circumferential channels, the blades follow a predetermined path that is a function of the position of the vacuum centering guide over the cornea and the arc and position of the dissector blades on the dissecting tool. The length of the blades can establish the length of the circumferential channels, or alternatively the surgeon can watch the dissector blade and stop it at or slightly past the furthest radial mark that the dissector blade can reach. Marks from the circumferential marker are helpful in assuring that the dissector blades follow their intended path.

The radial pocket markers, incision markers, and circumferential channel markers are shaped to conform to the cornea. Consequently, these markers have curved faces that generally follow the curved shape of the cornea so that at least substantially all of the marking faces of these markers apply dye to the patient's cornea.

A corneal marker which has at least one incision marker, at least one radial pocket marker, and a positioner provides incision and radial pocket marks on the patient's cornea in the positions where surgery is to occur. The surgeon only needs to press the corneal marker of FIGS. 7 or 8 to the patient's cornea once to mark the cornea with all of the marks the surgeon requires to perform the surgery described above. Surgical marks are correctly aligned to one another, which increases the reliability and accuracy of surgery.

Corneal Pocketing Tool

Once the incision has been made, (such as by using any appropriate surgical or diamond blade typically having a footplate on one or both sides of the blade to control the overall depth of the incision) pocketing between corneal layers may be accomplished using a suitable instrument, such as a dissector or spreader as described in copending U.S. application Ser. No. 08/896,792 filed on Jul. 18, 1997 titled "OPTHALMOLOGICAL INSTRUMENTS AND METHODS OF USE" the entirety of which is herein incorporated by reference.

Figure 11:
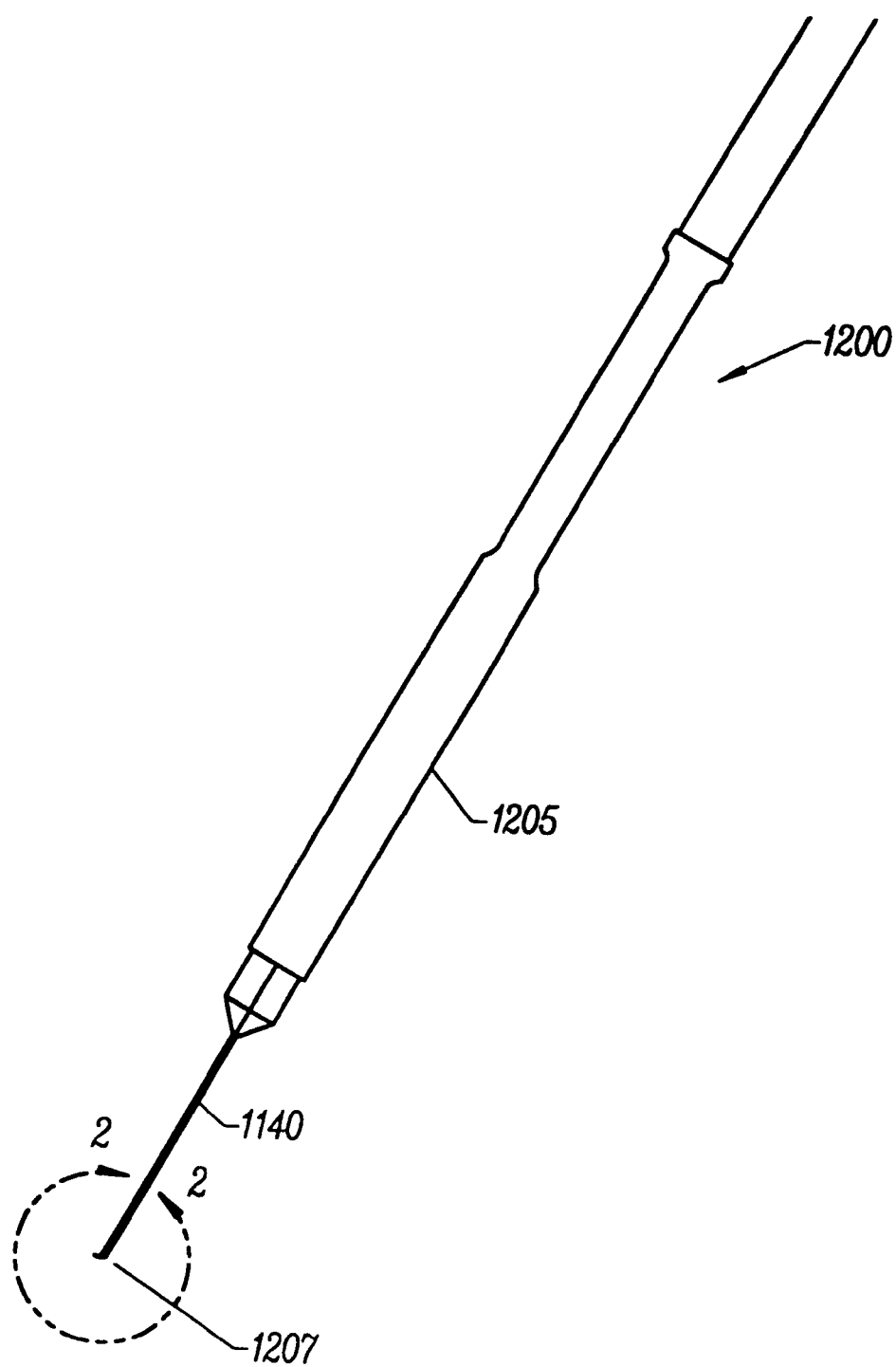
Figure 12:
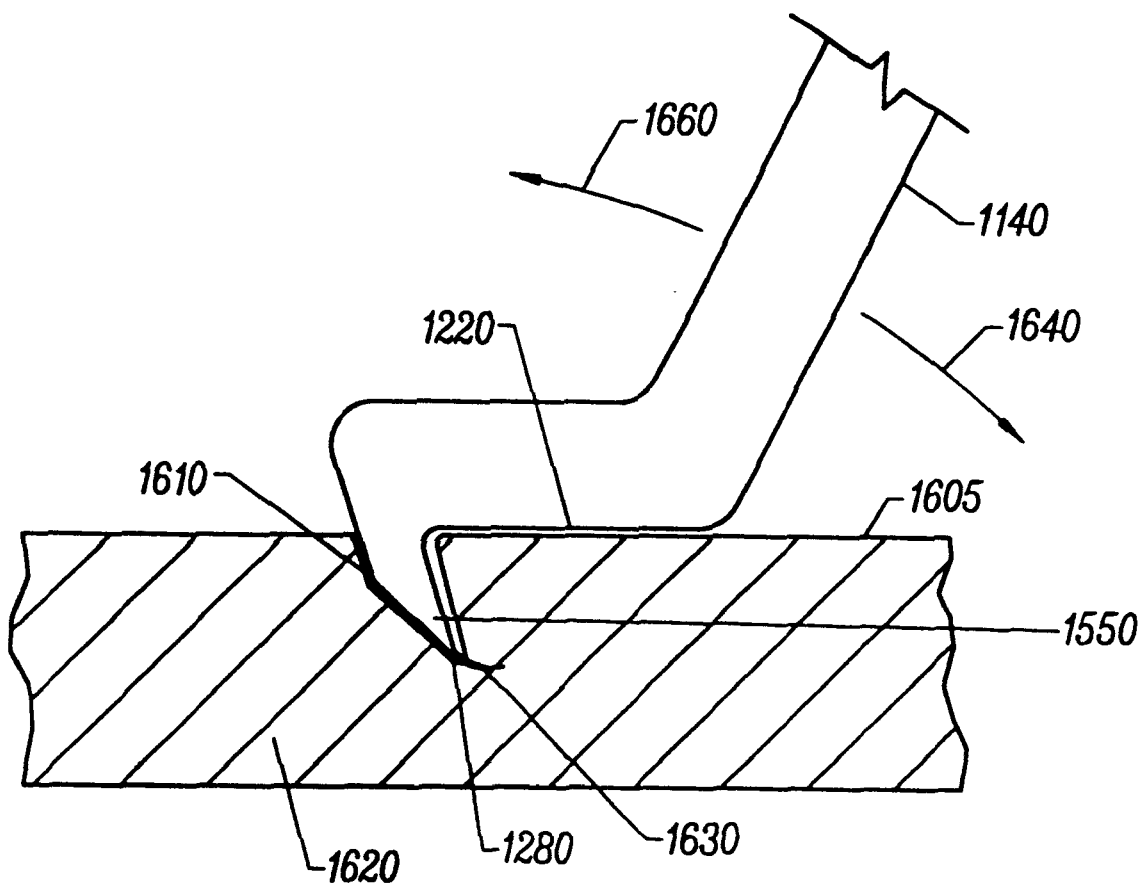

A specialized pocketing tool, such as those described in co-pending U.S. application U.S. application Ser. No. 08/993,445, titled "CORNEAL POCKETING TOOL", filed on Dec. 18, 1997, the entirety of which is herein incorporated by reference, may also be used to separate the stromal layers at the appropriate depth at the base of the incision. Pocketing tool (1200), as illustrated in FIGS. 11–12, has an instrument handle (1205), a thin instrument shaft (1140), terminating distally in tip section (1207). Tip section (1207) is shown more clearly inserted into an incision (1610) in FIG. 12. Tip section (1207) or pocketing tool (1200) has a reference surface or region (1220) constructed to contact the surface of the cornea (1605). Reference region (1220), when in contact with the surface of the cornea (1605) ensures that the distal-most tip (1280) of the dissector or spreader section (1550) is adjacent to the base of the incision (1610).

With the instrument in place as shown, the pocketing tool can be rotated in the direction of the arrow (1660) to create an intrastromal separation or pocket (1630). This small starter pocket may be enlarged as desired using a stromal spreader such as is described in co-pending U.S. application Ser. No. 08/896,792 filed on Jul. 18, 1997 titled "OPTHALMOLOGICAL INSTRUMENTS AND METHODS OF USE", and described below with reference to FIGS. 13–14B.

Spreader 150 includes handle 152, extension 154, and tip 156. To provide increased rotational control of spreader 150, a portion of handle 152 is knurled and cutouts 153 are provided in opposing positions for marking the instrument. Extension 154 has a much smaller outside diameter than handle 152, and has a tapering outside diameter that gradually decreases toward the end of extension 154 that joins with tip 156.

Tip 156 is substantially flat and relatively wide and thin as observed in a comparison of FIGS. 36A and 36B. Tip 156 extends from extension 154 at an obtuse angle $\beta$ to the longitudinal axis of extension 154 and handle 152, as shown in FIG. 36A. The obtuse angle provides the user with a comfortable handle position when tip 156 is inserted into the incision. Tip 156 has a tapering thickness t which decreases in the direction from the extension 154 to tip end 158.

As shown in FIG. 13B, tip end 158 is rounded and is preferably substantially hemispherical. although greater and lesser radii of curvature may be employed to define the tip end. Importantly, the tip end is not knife sharp, but rather, is relatively blunt so as to function to separate tissue along layers, but not to cut. Tip end 158 transitions into tip sides 160 as the curvature of tip end 158 gradually straightens into the substantially straight edges of tip sides 160. Tip sides 160 are sharp, although not knife sharp. A comparison of the relatively dull edge of tip end 158 and the relatively sharp edges of tip sides 160 can be seen by comparing the sectional views of FIGS. 13C and 13D, respectively.

With the arrangement of stromal spreader tip 156 as described, the relatively dull, slightly rounded tip end 158 greatly reduces the risk of perforation of the corneal tissues upon insertion of the tip into the incision. Additionally, by rotating the spreader using handle 152 the stromal layers are can be effectively separated to form a pocket, or enlarge or otherwise modify an initial pocket created by the corneal pocketing tool described above.

FIG. 13E illustrates, in an exaggerated way, the transition between blunt tip end 158 and the relatively sharp edge of tip side 160, which supports the fact that the insertion of the tip presents a relatively low risk of perforation of the stromal tissues. Once the spreader has been inserted, separation can begin through use of sharper side edges 160, together with blunt tip end 158.

FIG. 13F shows a variation of the tip shown in FIG. 13A. In this variation, the joinder of tip 156 and extension 154 is formed at the obtuse angle $\beta$ to the longitudinal axis of extension 154 and handle 152, the same as shown in FIG. 13A. However, the majority of the tip that is distal to the joinder of the tip and the extension, i.e., tip 156' is formed at an angle $\gamma$ with regard to the longitudinal axis of extension 154 and handle 152, and where angle $\gamma$ is an obtuse angle that is less than obtuse angle $\beta$. The remaining features of tip 156' are essentially the same as those described above with regard to tip 156 in FIGS. 13A–13E.

Figure 14B:
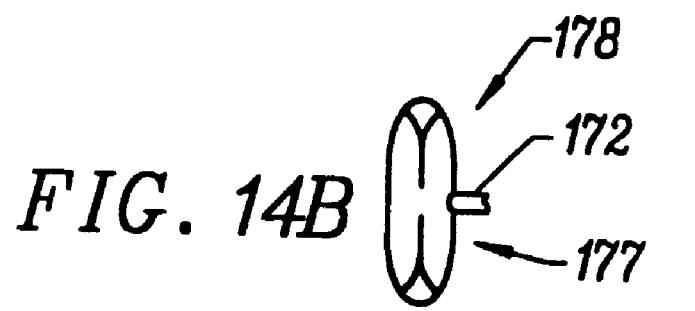
Figure 14A:
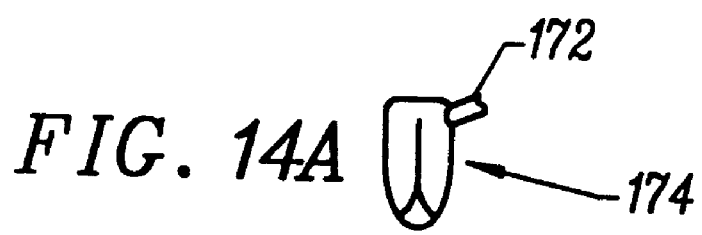
Figure 14C:
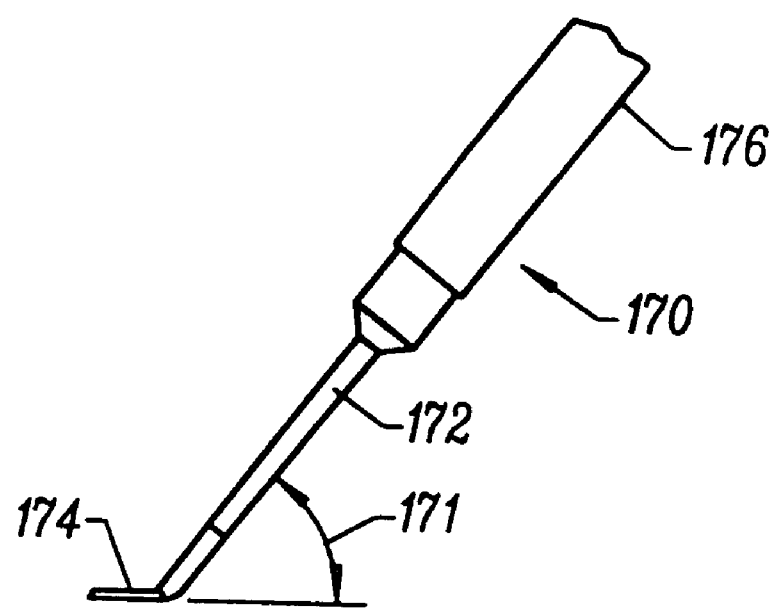

Preferably, the handle is oriented relative to the tip in such a way as to provide the surgeon with optimal visual and manual access to the surgical site. FIGS. 14A–14B illustrate an alternative handle orientation.

FIGS. 14A and 14B show partial top views of spreader 170 (generally shown in FIG. 14C) illustrating a single spreader tip construction 174 and a double spreader tip construction 177,178 respectively. Because the single tip construction is asymmetrical, it may be desirable to have two opposite-handed instruments available for use depending on surgeon preference. The construction of FIG. 14B eliminates this need for two separate instruments. The spreader tips of FIGS. 14A–14B may have any of the constructions described above.

Once the initial separation or pocket has been created in the manner described above, the surgeon inserts a clockwise dissector blade into the vacuum centering guide, and using a blunt-tipped instrument inserted into one of the small "starter" pockets, lifts the corneal tissue, and inserts the tip of the dissector blade into the starter pocket. The surgeon then rotates the dissector blade, which separates stroma and forms a clockwise circumferential channel between stroma. The surgeon removes the clockwise dissector blade and repeats the procedure using the counter-clockwise dissector blade to form a counter-clockwise circumferential channel. Separate, unjoined circumferential channels of any arc length or a continuous 360° channel can be formed using this method.

Radial Pocket-forming Instrument

The radial pocket-forming instrument as illustrated in FIG. 9 has a clockwise generally arcuate member 910, a tissue separator 920 on the generally arcuate member, and a handle 930 located at one end of the generally arcuate member. The radial pocket-forming instrument is inserted into a circumferential channel through the incision or incisions made to form the channel. The generally arcuate member follows the shape of the circumferential channel, so that the radial pocket-forming instrument can be inserted into the circumferential channel a distance that is sufficient to position the tissue separator at a site where a radial pocket is to be formed. The tissue separator is then pressed against a sidewall of the circumferential channel to separate stroma and form a radial pocket. The tissue separator is positioned generally on a radius through the center of the patient's pupil, and the tissue separator faces away from (as illustrated in FIG. 9) or toward the patient's pupil.

A circumferential channel typically has a radius of curvature of about or in excess of 3 mm at its edge closest to the pupil, and the circumferential channel typically has a radius of curvature of no more than about 5 mm on its edge furthest from the pupil. The generally arcuate member in this instance will have a radius of curvature of at least about 3 mm on its one side and less than about 5 mm on its other side, so that the generally arcuate member follows the shape of the circumferential channel.

Preferably, the radial pocket-forming instrument does not widen the circumferential channel as the instrument is positioned within the circumferential channel prior to forming a radial pocket. Consequently, the radial pocket-forming instrument of FIG. 9 has a width that is about equal to or is less than the width of the circumferential channel into which the instrument is inserted. The width of the instrument is the width of the generally arcuate member and the width of any tissue separator located at the site where the width of the generally arcuate member is measured. The width of the instrument is usually less than about 0.5 mm.

Clockwise and counter-clockwise radial pocket-forming instruments can be used to form the radial pockets when a single incision is used to form a circumferential channel or channels located on both sides of the single incision. A clockwise instrument has a generally arcuate member that travels in a clockwise direction from the handle to the tip of the instrument when viewing the generally arcuate member from directly above the handle of the instrument. A clockwise instrument can be inserted into a circumferential channel which was formed using a clockwise dissector blade.

The generally arcuate member of the radial pocket-forming instrument has an arc-length measured from the center of the tissue separator. This arc-length must be sufficiently long that the tissue separator is able to reach the desired distance from the incision so that it can form a radial pocket at the desired site or sites around the channel. For example, in the instance where six equidistantly-spaced radial pockets are formed and a single incision is spaced equidistantly between two adjacent radial pockets, the arc-length of a generally arcuate member must be at least about 330° when the radial pocket-forming instrument has only one tissue separator. The arc-length does not have to be any more than about 150° when clockwise and counter-clockwise instruments are used to form six radial pockets.

Alternatively, a number of radial pocket forming tools may be provided, each having an arc length only slightly longer than the distance to where a radial pocket is to be formed. For example, if inserts are to be placed every 60° from the initial incision, radial pocket forming tools having arc lengths in increments of 60° (about 30°, 90°, and 150°) would be provided. This advantageously prevents the surgeon from having to attempt to manipulate a pocket forming tool that has a large portion of its arc length outside of the incision.

The radial pocket-forming instrument can have more than one tissue separator on the generally arcuate member. The radial pocket-forming instrument can have, for example, as many tissue separators on the generally arcuate member as radial pockets that are to be formed in the portion of the circumferential channel in which the radial pocket-forming instrument will be inserted. The tissue separators will be located at positions on the generally arcuate member which correspond to the positions of the radial pockets when one of the tissue separators is aligned with the site where a radial pocket is to be formed. For example, in the instance where six equidistantly-spaced radial pockets are formed and a single incision is spaced equidistantly between two adjacent radial pockets, three tissue separators are located on e.g. a clockwise radial pocket-forming instrument at arc-lengths of about 30°, 90°, and 150°.

The tissue separator forms the radial pocket in or between stroma to allow the radial insert to be implanted therein. The tissue separator has a size and shape that are sufficient to form a radial pocket which holds at least a portion of the radial insert selected by the surgeon for implantation into that radial pocket. The tissue separator can be a blunt blade which separates stroma to allow insertion of the radial insert. Or, the tissue separator can be a sharp blade that cuts into the stroma, if the surgeon determines it is desirable to implant the radial insert into stroma. The tissue separator can be formed at an angle between e.g. about 20° and about 50° to the generally arcuate member to allow the tissue separator to better follow the curved contour of the stroma.

The tissue separator can form a radial pocket that has an angle intermediate between a radius drawn through the center of the cornea and a second line which is both tangential to the circumferential channel and perpendicular to the radius drawn through the center of the cornea. Thus, a radial pocket may not be located on a true radius from the center of the cornea but may, instead, be angled with regard to the true radius.

Positioning Instrument

The positioning instrument fits within a circumferential channel and engages a radial insert to maneuver the insert into a radial pocket. The clockwise positioning instrument illustrated in FIG. 10 has a generally arcuate member 1010, a tip 1020 positioned on the generally arcuate member, and a handle 1030 at one end of the generally arcuate member.

The size and shape of the generally arcuate member of the positioning instrument are very similar to the generally arcuate member of the radial pocket-forming instrument. The generally arcuate member of the positioning instrument has a width and shape which allow the generally arcuate member to be inserted into a circumferential channel without enlarging the channel significantly. Thus, the width of the member is about equal to or less than the width of the circumferential channel into which the generally arcuate member is to be placed, and in the embodiment illustrated in FIG. 10, the member is no more than about 0.5 mm wide. The generally arcuate member also has about the same radius of curvature as the circumferential channel, as described previously.

Figure 10:
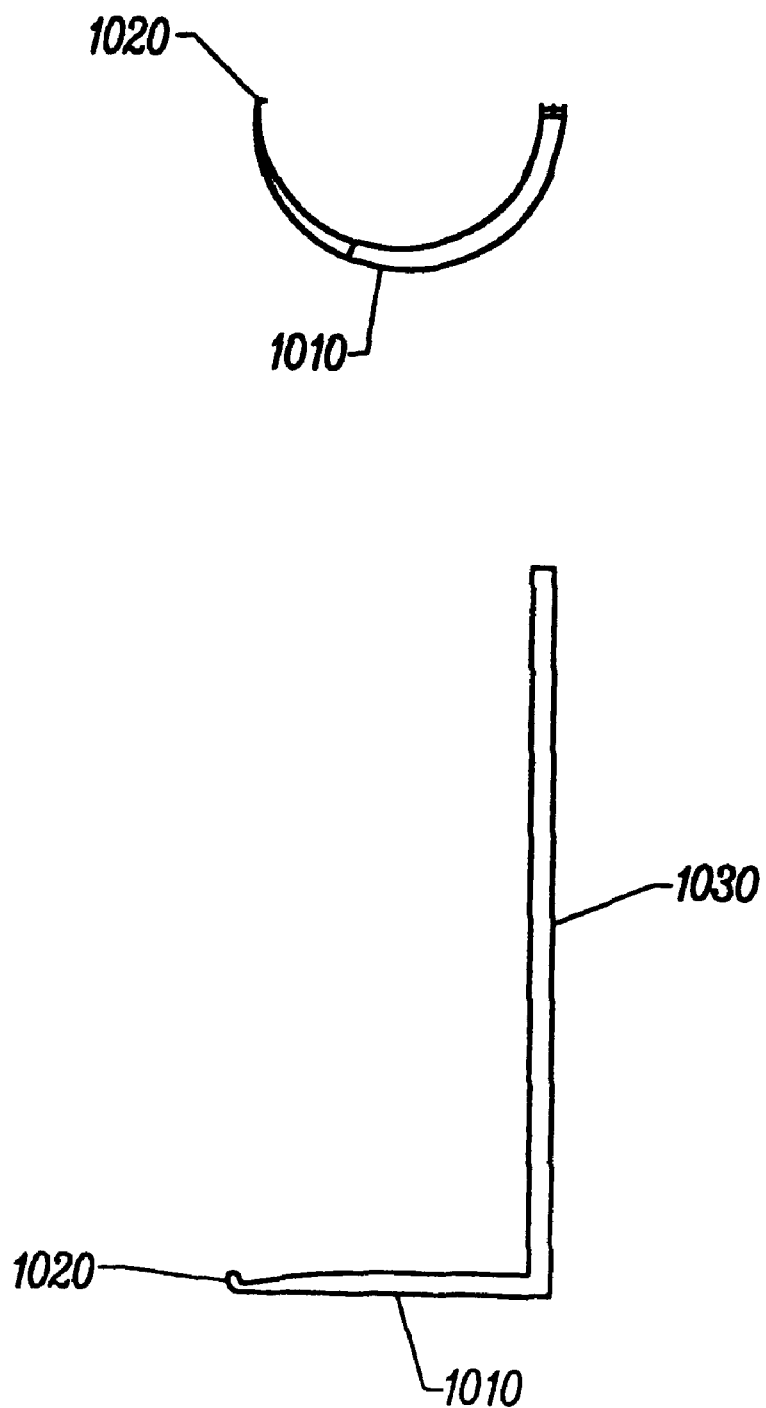
FIG. 10 illustrates a positioning instrument.

The tip 1020 on the positioning instrument is usually positioned at an end of the generally arcuate member. In FIG. 10, the tip is illustrated as a blunt end on a tapered wire forming the generally arcuate member, which wire was bent to an angle of about 90° to the plane of the generally arcuate member. The tip can be formed at any angle that allows the tip to maneuver the radial insert. The tip can be formed at an angle between 45° and 135°, for instance, and the tip can be bent upward or downward. The tip should be tall enough that the tip engages with a corner or side of a radial insert, so that the surgeon can coax or maneuver the radial insert into a radial pocket. The tip is preferably kept short so that the tip does not unduly drag against stroma as the positioning instrument is moved about in the circumferential channel. A tip height of 0.010–0.020 mm is sufficient to engage a radial insert to position it within a radial pocket. The tip may be smooth, or the tip may have small burrs or additional appendages such as arms which help to engage the radial insert when maneuvering it.

Clockwise and counter-clockwise positioning instruments can be supplied where a circumferential channel or channels extend on both sides of an incision into the cornea. The generally arcuate members of these instruments will typically have an arc length of 180° or less. As noted above, in the instance where six equidistantly-spaced radial pockets are formed and a single incision is spaced equidistantly between two adjacent radial pockets, a positioning instrument will have a generally arcuate member of an arc-length of no less than about 30°, and preferably the arc length is at least 90° or 150° so that the instrument can reach pockets that are distant from the incision.

Of course, as noted above with regard to the pocket forming tool, a number of arcuate members may be provided, each having an arc length to extend a desired distance from the initial incision. Preferably, the arc length of the arcuate member of the positioning instrument will be a little longer than the distance from the incision to the radial pocket of interest. For example, with radial pockets at 30°, 90° and 150°, arc lengths for the arcuate member of the positioning instrument may be 50°, 110°, and 170°. The added length is useful in case a segment is pushed beyond the radial pocket and it is necessary to hook on the far side of the insert to pull it back, towards the incision.

The corneal marker has seven radial pocket markers where seven radial inserts are placed within the patient's eye. The radial pocket markers are positioned 360°/7 or about 51.4° from one another, and the generally arcuate members of the clockwise and counter-clockwise radial pocket-forming instruments have a length at least about 25° and no more than about 155°.

The corneal marker has eight radial pocket markers where eight radial inserts are placed within the patient's eye. The radial pocket markers are positioned about 45° from one another, and the generally arcuate members of the clockwise and counter-clockwise radial pocket-forming instruments have a length at least about 22.5° and no more than about 157.5°.

What is claimed is:

1. A radial pocket-forming instrument for insertion into a circumferential channel within a cornea of a patient's eye and for forming a radial pocket connected to the circumferential channel, said radial pocket-forming instrument comprising a generally arcuate member and a tissue separator blade extending radially from the generally arcuate member, wherein the tissue separator blade is adapted to create a radial pocket connected to the circumferential channel when the tissue separator blade is engaged with a sidewall of the circumferential channel.

2. The radial pocket-forming instrument of claim 1, wherein the tissue separator blade is positioned on the pocket-forming instrument so that the tissue separator blade forms said radial pocket in the stroma in a direction toward the pupil of the patient's eye when the radial pocket-forming instrument is inserted into the circumferential channel and is used to form the radial pocket.

3. The radial pocket-forming instrument of claim 1, wherein the tissue separator blade is positioned on the pocket-forming instrument so that the tissue separator blade forms said radial pocket in the stroma in a direction away from the pupil of the patient's eye when the radial pocket-forming instrument is inserted into the circumferential channel and is used to form the radial pocket.

4. The radial pocket-forming instrument of claim 1, wherein the generally arcuate member has an inner radius of curvature greater than about 3 mm.

5. The radial pocket-forming instrument of claim 1, wherein the generally arcuate member has an outer radius of curvature of no more than about 5 mm.

6. The radial pocket-forming instrument of claim 1, wherein the generally arcuate member has an arc length of no more than about 155°.

7. The radial pocket-forming instrument of claim 1, wherein the generally arcuate member has an arc length of greater than about 25°.

8. The radial pocket-forming instrument of claim 1, wherein the instrument further comprises a handle positioned on an end of the generally arcuate member.

9. The radial pocket-forming instrument of claim 1, wherein the tissue separator blade is blunt.

10. The radial pocket-forming instrument of claim 1, wherein the instrument has a width such that the tissue separator blade of the instrument clears the sidewall of the circumferential channel as the instrument is withdrawn from the circumferential channel.

11. The radial pocket-forming instrument of claim 1, wherein the tissue separator blade is angled with respect to the side of the generally arcuate member so that the tissue separator blade forms the radial pocket in the same stromal plane as the generally arcuate member when the instrument is used to form the radial pocket.

12. A radial pocket-forming instrument for insertion into a circumferential channel within a patient's cornea and for forming a radial pocket connected to the circumferential channel, said radial pocket-forming instrument comprising a curved body means adapted to fit within the circumferential channel and a cutting blade extending radially from the curved body means, wherein the cutting blade is adapted to form a radial pocket when the cutting blade engages a sidewall of the circumferential channel.

13. The radial pocket-forming instrument of claim 12 wherein the body means is adapted to enter the circumferential channel through a single opening into the circumferential channel from the exterior of the eye.

14. A system for forming radial pockets in a clockwise circumferential channel and a counter-clockwise circumferential channel, said system comprising the radial pocket-forming instrument of claim 1, wherein the generally arcuate member of said instrument is a clockwise arcuate member, and a second radial pocket-forming instrument of claim 1, wherein the generally arcuate member of said second instrument is a counter-clockwise arcuate member.

* * * * *